(12) United States Patent
Hines et al.

(10) Patent No.: US 6,459,920 B1
(45) Date of Patent: Oct. 1, 2002

(54) METHOD FOR DETECTING AND DIAGNOSING EPITHELIAL CANCER

(75) Inventors: Joseph Hines, Paradise Valley, AZ (US); Ralph E. Green, Scottsdale, AZ (US)

(73) Assignee: Zila, Inc., Phoenix, AZ (US)

( * ) Notice: Subject to any disclaimer, the term of this patent is extended or adjusted under 35 U.S.C. 154(b) by 0 days.

(21) Appl. No.: 09/262,555

(22) Filed: Mar. 4, 1999

Related U.S. Application Data

(63) Continuation-in-part of application No. 08/553,377, filed as application No. PCT/US94/01918 on Feb. 16, 1994, now abandoned.

(51) Int. Cl.[7] .................................................. A61B 5/05
(52) U.S. Cl. ......................... 600/407; 348/77; 424/9.1; 128/920; 128/922
(58) Field of Search ................................ 600/109, 110, 600/111, 112, 407; 348/77, 66, 69, 74, 65; 424/9.1; 396/16, 17; 128/920, 922, 923

(56) References Cited

U.S. PATENT DOCUMENTS

| | | | | |
|---|---|---|---|---|
| 5,115,307 A | * | 5/1992 | Cooper et al. | 358/98 |
| 5,251,613 A | * | 10/1993 | Adair | 128/6 |
| 5,291,889 A | * | 3/1994 | Kenet et al. | 128/653.1 |
| 5,528,432 A | * | 6/1996 | Donahoo | 359/894 |
| 5,745,165 A | * | 4/1998 | Atsuta et al. | 348/65 |
| 5,845,639 A | * | 12/1998 | Hochman et al. | 128/653.1 |
| 5,993,378 A | * | 11/1999 | Lemelson et al. | 600/109 |
| 6,032,678 A | * | 3/2000 | Rottem | 128/920 |

OTHER PUBLICATIONS

Galante et al., Tumors of the Head & Neck, 1981.*

* cited by examiner

Primary Examiner—Marvin M. Lateef
Assistant Examiner—Eleni Mantis Mercader
(74) Attorney, Agent, or Firm—Drummond & Duckworth

(57) ABSTRACT

A method for detecting epithelial cancer includes generating a real-time video image of the locus of potential cancerous sites on the epithelium. The real-time video image is displayed on a television monitor screen. The real-time video image on the monitor is examined to locate suspected cancerous sites and the results of such examination are recorded.

2 Claims, 1 Drawing Sheet

METHOD FOR DETECTING AND DIAGNOSING EPITHELIAL CANCER

CROSS-REFERENCE TO RELATED APPLICATION

This Application is a Continuation-in-Part of U.S. application Ser. No. 08/553,377, filed Feb. 22, 1996, now abandoned which is a national stage application, filed under 35 U.S.C. §371, derived from corresponding International Application PCT/US94/01918 (WIPO Publication WO05/22279), filed Feb. 16, 1994.

BACKGROUND OF THE INVENTION

1. Field of the Invention

This invention relates to methods for detecting and diagnosing epithelial cancer.

More particularly, the invention relates to a cancer detection method employing video technology for real-time examination of potential cancerous sites on the epithelium, combined with comparison of a digitized image of a suspect site with digitized images of known cancerous and non-cancerous sites, to effect a diagnosis of the suspect sites.

In another aspect, the invention relates to real-time videographic examination techniques in combination with in vivo tissue staining techniques and with digitized image techniques for the diagnosis of epithelial cancer.

In an even further and still more particular respect, the invention relates to cancer detection/diagnosis techniques in which videographic records of the visual image of a suspected cancer site on the epithelium are compared with a real-time videographic image of the suspected site which is made at a later time.

In a further aspect the invention relates to cancer detection/diagnosis techniques in which digitized videographic images of a suspected cancerous site on the epithelium is compared with digitized images in a data base containing images of both cancerous and non-cancerous epithelial lesions.

2. Description of Related Art

Visual examination of epithelial tissue to detect cancerous or pre-cancerous tissue is known. In vivo examination of suspected cancerous sites using standard photographs, magnification by an operating microscope (stomatoscopy) and color photomicrographs for the detection of oral cancer was described in the article by Shedd, et al., American Journal of Surgery, Volume 110, pages 631 et seq. (October 1965).

Dental television cameras which facilitate visualization of the oral cavity are also well known. See, e.g., the U.S. Pat. No. 4,260,376 to Litel; U.S. Pat. No. 4,195,626 to Lemmey and U.S. Pat. No. 5,251,023 to Cooper. Apparatus and methods for recording in vivo holograms and for reconstructing such recorded holograms for later display on a television monitor were described by Bjelkhagen. et al. in U.S. Pat. No. 5,014,709.

The use of biological stains for in vivo selective delineation of cancerous and pre-cancerous tissue is also well known. See, e.g., U.S. Pat. No. 4,321,251 to Mashberg and the article by Nibel (Journal of American Dental Association, Volume 35, pages 801 et seq. (June, 1964)). Shedd, supra, discloses the use of selective tissue staining techniques in combination with stomoatoscopy.

Cancer of the oral mucosa is one of the leading terminal diseases causing thousands of deaths annually in the United States alone. Oral cancers occur at various places in the oral cavity, including the floor of the mouth, the anterior pillars, on the pallet and on the bottom and the dorsum of the tongue. Most oral cancers are curable by surgical excision if detected early enough. However, the difficulty of visualizing the various intraoral epithelial surfaces makes it difficult to detect oral cancers in the very early stages. It is particularly difficult to detect pre-cancerous sites in the oral cavity, because of the difficulty in visualizing the physically remote oral epithelium coupled with the confusingly similar appearance of precancerous tissues with tissue having other, non-cancerous conditions.

While video technology and equipment has been available for a number of years which enables dental practitioners to visualize intraoral tissue in order to facilitate conventional dental procedures and while tissue staining techniques have been known for many years which selectively stain and visually delineate cancerous epithelial tissue and plaque and while photographic, holographic and other techniques have been known for recording visual images for later examination, such techniques have not been effectively employed to provide straightforward real-time diagnostic visual examination of the intraoral epithelium for detection of oral cancers and pre-cancerous conditions.

It would be highly desirable to provide improved methods for detecting epithelial cancers, particularly oral cancers.

It would also be advantageous to provide such methods which can be effectively employed by general dental practitioners as a part of routine dental procedures or "check-ups" or as an adjunct to routine periodic dental office visits for plaque removal and the like. Such improved oral cancer detection methods could result in early detection of oral cancer and timely therapy, saving many thousands of lives annually.

SUMMARY OF THE INVENTION

Accordingly, the principal object of the present invention is to provide an improved method for early detection of epithelial cancer, particularly oral cancers, including single or multiple small or large sites.

Yet another object of the invention is to provide such improved methods which can be used effectively by general dental practitioners, with a minimum of additional training and expense, to provide routine oral cancer screening services as an adjunct to routine dental procedures and examinations.

Still another object of the invention is to provide oral cancer screening techniques which permit real-time examination of remotely located epithelial tissues in the oral cavity, which are difficult to examine by conventional visual examination techniques.

Still another and further object of the invention is to provide real-time cancer detection techniques which, nevertheless, provide a permanent record of the results of such an examination, so as to permit comparative examination of the present image of a suspected cancer site with images of the same site made at an earlier time.

A still further object of the invention is to provide an epithelial cancer detection and delineation method which provides a visual record for later reference during therapy, e.g., to aid in excision surgery.

Yet another object of the invention is to provide a method for determining whether a suspected cancerous site on the epithelium is cancerous or non-cancerous, employing a comparison of a digitized videographic image of the suspected site with digitized images known cancerous and non-cancerous epithelial lesions.

BRIEF DESCRIPTION OF THE DRAWING

Those and other, further and more specific objects and advantages of the invention will be apparent to those skilled in the art from the following detailed description thereof, taken in conjunction with the drawing in which.

Figure 1:
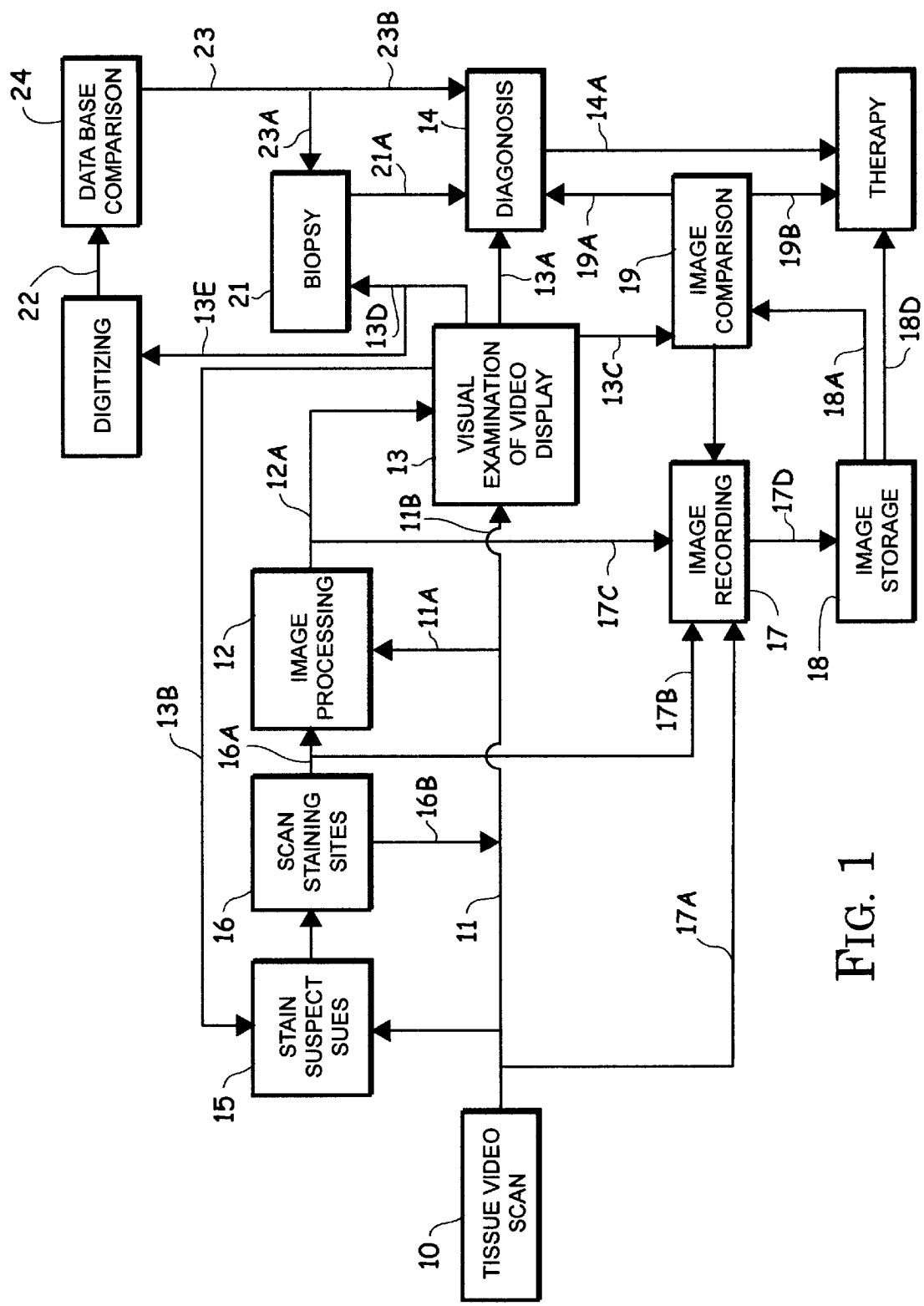
FIG. 1 is a flow sheet illustrating various embodiments of the method of the present invention, and the best mode presently known for the practice thereof.

Briefly, in accordance with the invention, I provide a method for detecting epithelial cancer which includes the steps of generating video signals which represent the real-time image of the locus of potential cancerous sites on the epithelium, displaying this real-time image on a television monitor screen, visually examining the displayed image to locate suspected cancerous sites, digitizing said real-time image of a suspected cancerous site and comparing the digitized image of the suspected site with digitized images in a data base of images of known cancerous and non-cancerous oral epithelial lesions. In a further preferred embodiment of the invention, the method also includes applying a biological stain to the epithelium, to selectively cancerous tissue. Other aspects of the best mode presently contemplated for practicing the present invention are disclosed in connection with the description of FIG. 1, set forth below.

The drawing is presented for purposes of illustrating the preferred practice of the invention, but is not intended as a limitation on the scope of the invention.

DESCRIPTION OF THE PREFERRED EMBODIMENTS

Referring to FIG. 1, according to my method a conventional dental video camera is used to make a preliminary scan 10 of the tissue which is the locus of potential cancerous sites on the epithelium. For example, a suitable video camera for use in accordance with my invention is disclosed in the patent to Cooper, et al. U.S. Pat. No. 5,241,025. The video image 11 from the scan 10 may be subjected to electronic image processing 12 (as indicated by the arrow 11a) or the image 11 can be directly utilized as indicated by the arrow 11b. Either the processed image 12a or the unprocessed image 11b is then displayed for visual examination 13 on a television monitor screen. If such visual examination 13 definitively reveals a cancerous site, as indicated by the arrow 13a, this may be directly employed to effect a diagnosis 14.

On the other hand, if the visual examination 13 does not yield a definitive diagnosis 14, but indicates suspect cancerous sites (as indicated by the arrow 13b), then a selective stain is applied 15 to the suspect sites and a second video scan 16 of the stained sites is made. For example, such selective stain compositions are included in diagnostic kits which are commercially available in certain countries under the trademark "ORASCAN", "ORASCREEN" and "ORATEST". The image from the second scan 16 is then either subjected to image processing as indicated by the arrow 16a or the unprocessed image 16b is displayed on a television monitor for visual examination 13. The visual examination of the processed or unprocessed image from the second scan 16 may also lead directly to a diagnosis 14.

The video signals representing the images formed by either the first scan 10 or the second scan 16, processed or unprocessed, are recorded 17, for example by a conventional video recorder, as indicated by the arrows 17a, 17b and 17c and the resultant records 17d are stored 18 for future reference.

Any of the visual examinations 13 may be facilitated by comparisons 19 of the real-time image 13c and a previously recorded stored image 18a of the same site to facilitate diagnosis 14, as indicated by the arrow 19a. Similarly, a visual examination 13 may indicate the necessity or desirability of a biopsy 21 as indicated by the arrow 13d, to confirm the diagnosis 14 as indicated by the arrow 21a. If the diagnosis 14 indicates that therapy is required as indicated by the arrow 14a, the therapy, for example, surgical excision can be facilitated, as indicated by the arrow 19b by a comparison 19 of the real-time image 13c with a stored image 18a or by direct reference to the stored image 18b.

Alternatively, in accordance with the presently preferred embodiment of the invention a real-time video image 11, which is determined by the visual examination 13 to be a suspected cancerous site, can be digitized, as indicated by the arrow 13e and the digitized image 22 of the suspected cancerous site is then compared 24 with a data base of digitized images of known cancerous and non-cancerous oral epithelial lesions, to determine with greater accuracy by shape, surface texture and topography whether the suspected site is cancerous or non-cancerous. The results 23b of the comparison may, therefore, directly yield a diagnosis 14 or, if the results are still questionable, the compared site 23a is subjected to conventional biopsy 21. The results of which 21a yield a diagnosis 14.

As used herein, the term "cancerous site" is intended to include both cancerous and precancerous tissues. The cancerous tissue may be in situ carcinomas or early-invasive carcinomas and the precancerous conditions include dysplastic tissues or lesions and neoplastic tissues or lesions as distinguished from the normal squamous epithelium.

The term "image processing" includes any of the known electronic image intensification techniques, including as for example, digital filtering, contrast enhancement, frequency analysis, 3-D rotation, digital magnification, threshold analysis and the like.

Having described my invention in such terms as to enable those skilled in the art to understand and practice it and having identified the presently preferred embodiments and best mode thereof, we claim:

1. A method for detection and diagnosis of epithelial intra-oral cancer, comprising:

a) generating first video signals representing the image of the locus of potential cancerous sites on the epithelium;

b) recording the first video signals;

c) generating second video signals representing the real-time image of the same locus of the potential cancerous sites on the epithelium at a date later than first video signals were generated;

d) contemporaneously displaying the first and second video signals next to each other on a television monitor screen; and e) visually comparing and examining the displayed images for detecting suspected cancerous sites.

2. The method of claim 1 which includes the step of applying a selective biological stain to the oral epithelium to selectively stain cancerous tissues.

* * * * *